(12) United States Patent
Zhang et al.

(10) Patent No.: US 7,720,196 B2
(45) Date of Patent: May 18, 2010

(54) TARGET TRACKING USING SURFACE SCANNER AND FOUR-DIMENSIONAL DIAGNOSTIC IMAGING DATA

(75) Inventors: Hui Zhang, Sunnyvale, CA (US); Dongshan Fu, Santa Clara, CA (US); Gopinath Kuduvalli, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 95 days.

(21) Appl. No.: 12/008,083

(22) Filed: Jan. 7, 2008

(65) Prior Publication Data

US 2009/0175406 A1 Jul. 9, 2009

(51) Int. Cl.
*A61N 5/10* (2006.01)
(52) U.S. Cl. ...................................................... 378/65
(58) Field of Classification Search .............. 378/4, 378/8, 63, 65; 382/131, 151
See application file for complete search history.

(56) References Cited

U.S. PATENT DOCUMENTS

| | | | |
|---|---|---|---|
| 6,144,875 | A | 11/2000 | Schweikard et al. |
| 6,522,712 | B1 * | 2/2003 | Yavuz et al. ................... 378/4 |
| 7,187,792 | B2 | 3/2007 | Fu et al. |
| 7,260,426 | B2 | 8/2007 | Schweikard et al. |
| 2005/0047544 | A1 | 3/2005 | Fu et al. |
| 2005/0180544 | A1 | 8/2005 | Sauer et al. |
| 2006/0002630 | A1 | 1/2006 | Fu et al. |
| 2006/0004281 | A1 | 1/2006 | Saracen |
| 2006/0074292 | A1 | 4/2006 | Thomson et al. |
| 2006/0074299 | A1 | 4/2006 | Sayeh |
| 2006/0274061 | A1 | 12/2006 | Wang et al. |
| 2007/0110289 | A1 | 5/2007 | Fu et al. |
| 2007/0127845 | A1 | 6/2007 | Fu et al. |
| 2007/0201613 | A1 | 8/2007 | Lu et al. |
| 2008/0170663 | A1 * | 7/2008 | Urano et al. .................. 378/65 |

OTHER PUBLICATIONS

E Coste-Maniere, D Olender, W Kilby, R A Schulz, Robotic whole body stereotactic radiosurgery: clinical advantages of the CyberKnife integrated system, Int J. Medival Robotics and Computer Assisted Surgery 2005;1(2):28-39, www.roboticpublications.com.
Surface Imaging International Ltd—Vectra 3D Scanner, product brochure, www.inition.co.uk Retrieved on Oct. 1, 2007.
International Search Report and Written Opinion of the International Searching Authority, PCT/US08/12274 filed Oct. 28, 2008, mailed Dec. 22, 2008.
Kamino et al., "Development of a Four-Dimensional Image-Guided Radiotherapy System with a Gimbaled X-Ray Head", Int. J. Radiation Oncology Biol. Phys., (2006) vol. 66, No. 1, pp. 271-278; Abstract.

* cited by examiner

*Primary Examiner*—Chih-Cheng G Kao
(74) *Attorney, Agent, or Firm*—Blakely, Sokoloff, Taylor & Zafman LLP

(57) ABSTRACT

A method and apparatus for tracking a pathological anatomy within a patient's body is described. A data model of a skin surface of the patient's body may be acquired using light reflected from the skin surface. The data model can be matched with skin surfaces reconstructed and/or interpolated from four-dimensional (4D) diagnostic imaging data, such as 4D CT data, to determine a temporal phase of the patient's respiratory motion. The identified temporal phase may then be used in conjunction with the diagnostic imaging data to identify a location of the pathological anatomy within the patient's body.

25 Claims, 11 Drawing Sheets

TARGET TRACKING USING SURFACE SCANNER AND FOUR-DIMENSIONAL DIAGNOSTIC IMAGING DATA

TECHNICAL FIELD

This invention relates to the field of radiation treatment, and in particular, to a system of tracking the movement of a pathological anatomy during respiration.

BACKGROUND

One challenge facing the delivery of radiation to treat pathological anatomies such as tumors or lesions is identifying the location of the target (i.e. tumor location within a patient). The most common technique currently used to identify and target a tumor location for treatment involves a diagnostic x-ray or fluoroscopy system to image the patient's body to detect the position of the tumor. This technique assumes that the tumor is stationary. Even if a patient is kept motionless, radiation treatment requires additional methods to account for movement due to respiration, in particular when treating a tumor located near the lungs. Breath hold and respiratory gating are two primary methods used to compensate for target movement during respiration while a patient is receiving conventional radiation treatments.

Breath hold requires the patient to hold his or her breath at the same point in the breathing cycle and only treats the tumor when the tumor is stationary. A respirometer is often used to measure the tidal volume and ensure the breath is being held at the same location in the breathing cycle during each irradiation. This method takes longer than a standard treatment and often requires training the patient to hold his or her breath in a repeatable manner.

Respiratory gating is the process of turning on the radiation beam as a function of a patient's breathing cycle. When using a respiratory gating technique, treatment is synchronized to the individual's breathing pattern, limiting the radiation beam delivery to only one specific part of the breathing cycle and targeting the tumor only when it is in the optimum range. This treatment method may be much quicker than the breath hold method but requires the patient to have many sessions of training to breathe in the same manner for long periods of time. This training requires many days of practice before treatment can begin. This system may also require healthy tissue to be irradiated before and after the tumor passes into view to ensure complete coverage of the tumor. This can add an additional margin of 5-10 mm on top of the margin normally used during treatment.

Attempts have been made to avoid the burdens placed on a patient from breath hold and respiratory gating techniques. In another method to track the movement of a tumor in real time during respiration, a combination of internal imaging markers and external position markers has been used to detect the movement of a tumor. In particular, fiducial markers are placed near a tumor to monitor the tumor location. The position of the fiducial markers is coordinated with the external position markers to track the movement of the tumor during respiration. External position markers are used because the fiducial markers are typically monitored with x-ray imaging. Because it may be unsafe to expose the patient continuously to x-rays to monitor the fiducials, the position of the markers can be used to predict the position of the fiducial markers between the longer periods of x-ray images. One type of external position markers integrates light emitting diodes (LEDs) into a vest that is worn by the patient. The flashing LEDs are then detected by a camera system to track movement.

BRIEF DESCRIPTION OF THE DRAWINGS

The present invention is illustrated by way of example, and not by way of limitation, in the figures of the accompanying drawings.

DETAILED DESCRIPTION

Described herein is a method and apparatus for tracking the movement of a pathological anatomy during respiration. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

According to an embodiment of the present invention, the motion of a pathological anatomy, such as a tumor, within the body of a patient may be tracked by acquiring a data model of a skin surface of the patient's body, then matching the data model with four-dimensional (4D) diagnostic imaging data, such as four-dimensional computed tomography (4D CT) data from the patient that includes the location of the pathological anatomy relative to the skin surface. During radiation treatment of the patient, the data model may be acquired by capturing light reflected from the surface of the patient's skin. For example, the data model of the patient's skin surface may be acquired using techniques such as laser scanning or photogrammetry.

According to this process, the data model can be compared with 4D diagnostic imaging data from the patient that includes the images of the pathological anatomy in order to track the motion of the pathological anatomy. The 4D data may include a series of three-dimensional representations of the patient's anatomy, each correlated with a temporal phase. The temporal phases may, for example, represent phases in the patient's respiratory cycle. Each of the three-dimensional representations of the patient's anatomy may describe the location of the pathological anatomy relative to the patient's skin surface. The data model of the patient's skin surface may then be matched with one or more of the three dimensional representations within the 4D diagnostic imaging data in order to determine the location of the pathological anatomy at the time the data model of the skin surface was acquired.

Figure 1A:
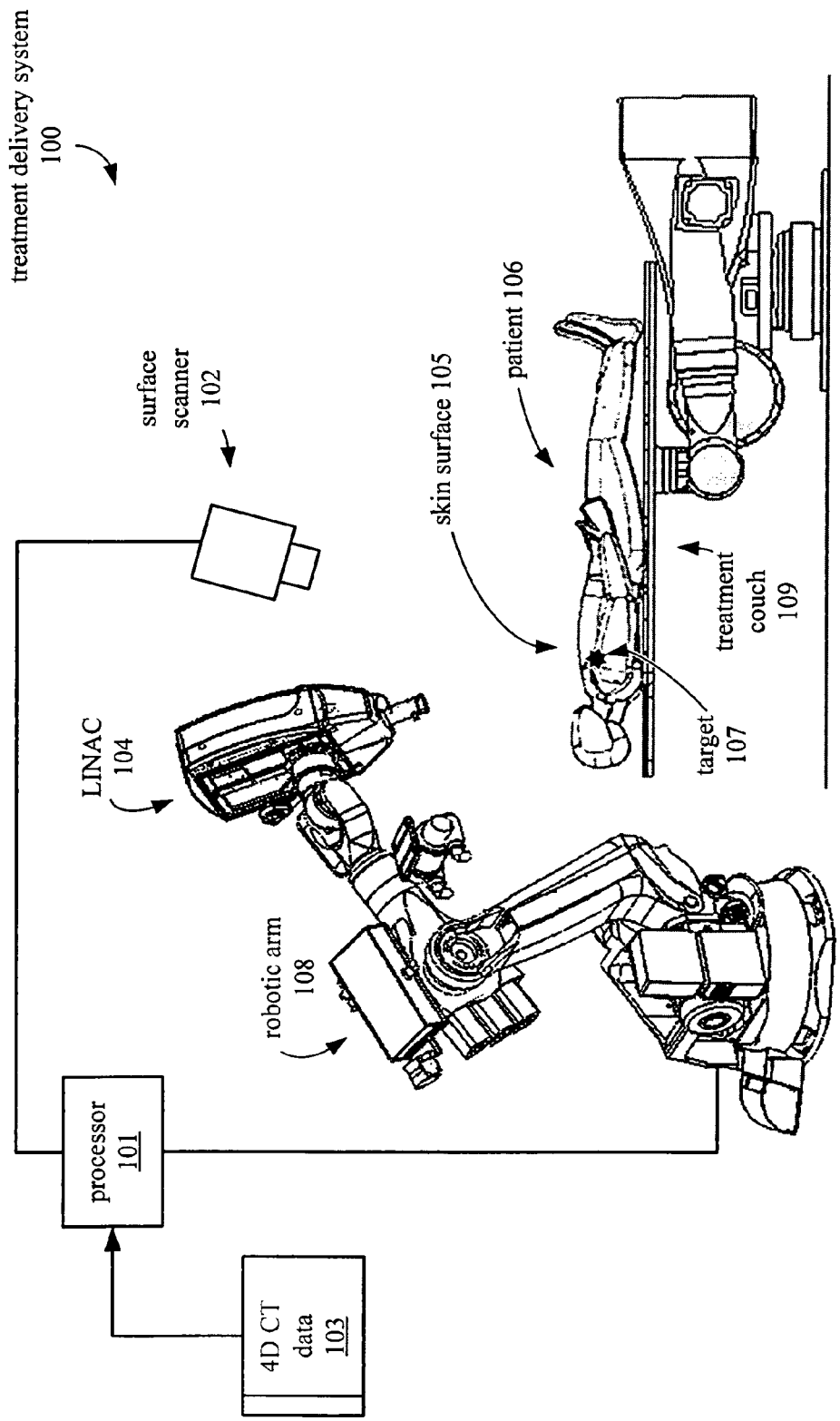
FIG. 1A illustrates a system for tracking motion of a target within the body of a patient and delivering treatment to the tracked target.

FIG. 1A illustrates a system for tracking motion of a pathological anatomy, such as a tumor, using four dimensional (4D) diagnostic imaging data and skin surface acquisition according to one embodiment of the invention. Treatment delivery system 100 includes processor 101, surface scanner 102 for acquiring a data model of skin surface 105 of patient 106, four dimensional computed tomography (4D CT) data 103, linear accelerator (LINAC) 104, and robotic arm 108. Motion tracking system can be used for tracking motion of a target 107 within patient 106, while the patient lies on treatment couch 109.

In treatment delivery system 100, processor 101 is connected with surface scanner 102 so that processor 101 may control operation of surface scanner 102 and receive data acquired by surface scanner 102. Surface scanner 102 may be any device capable of acquiring data that can be used to produce a data model of skin surface 105 of the patient 106. For example, surface scanner 102 may be a laser scanner or a digital surface photogrammetry system, such as the Vectra 3D Scanner produced by Surface Imaging International, Ltd. Processor 101 also has access to four-dimensional computed tomography (4D CT) data 103. 4D CT data 103 may have been acquired from a 4D CT scanner. The 4D CT data may be stored on a magnetic disk or other computer-readable medium. In alternative embodiments, 4D CT data 103 may be replaced with other forms of diagnostic imaging data. For example, 4D CT data 103 may be replaced with a data model that was acquired by means other than computed tomography. Processor 101 may be further connected to linear accelerator (LINAC) 104, which is capable of producing a radiation beam suitable for radiation treatment. Processor 101 may be connected to LINAC 104 so that processor 101 can control the output and other aspects of operation of LINAC 104. Processor 101 may also be configured to receive information from LINAC 104, such as status information. LINAC 104 may be mounted on a robotic arm 108 that can be controlled by processor 101. Robotic arm 108 may provide processor 101 with the ability to direct the beam of LINAC 104 at different locations and from different angles.

Surface scanner 102 may be positioned to acquire a data model of skin surface 105 which lies over target 107. This data model can then be transmitted to processor 101, which compares the data model with 4D CT data 103. Based on the comparison between the acquired data model and 4D CT data 103, processor 101 determines the position of target 107. Processor 101 can then direct robotic arm 108 to move so that the beam of LINAC 104 intersects target 107. In one embodiment, target 107 is a pathological anatomy such as a tumor. Alternatively, target 107 may be any subject for which location tracking is desired. By repeating the process of acquiring a data model of skin surface 105, comparing the data model to 4D CT data 103, determining the location of target 107, then moving robotic arm 108 so that the beam of LINAC 104 intersects with target 107, processor 101 may track the location of target 107 continuously and maintain the beam of LINAC 104 directed at the target for the duration of a radiation treatment session, even while the target is moving.

Figure 1B:
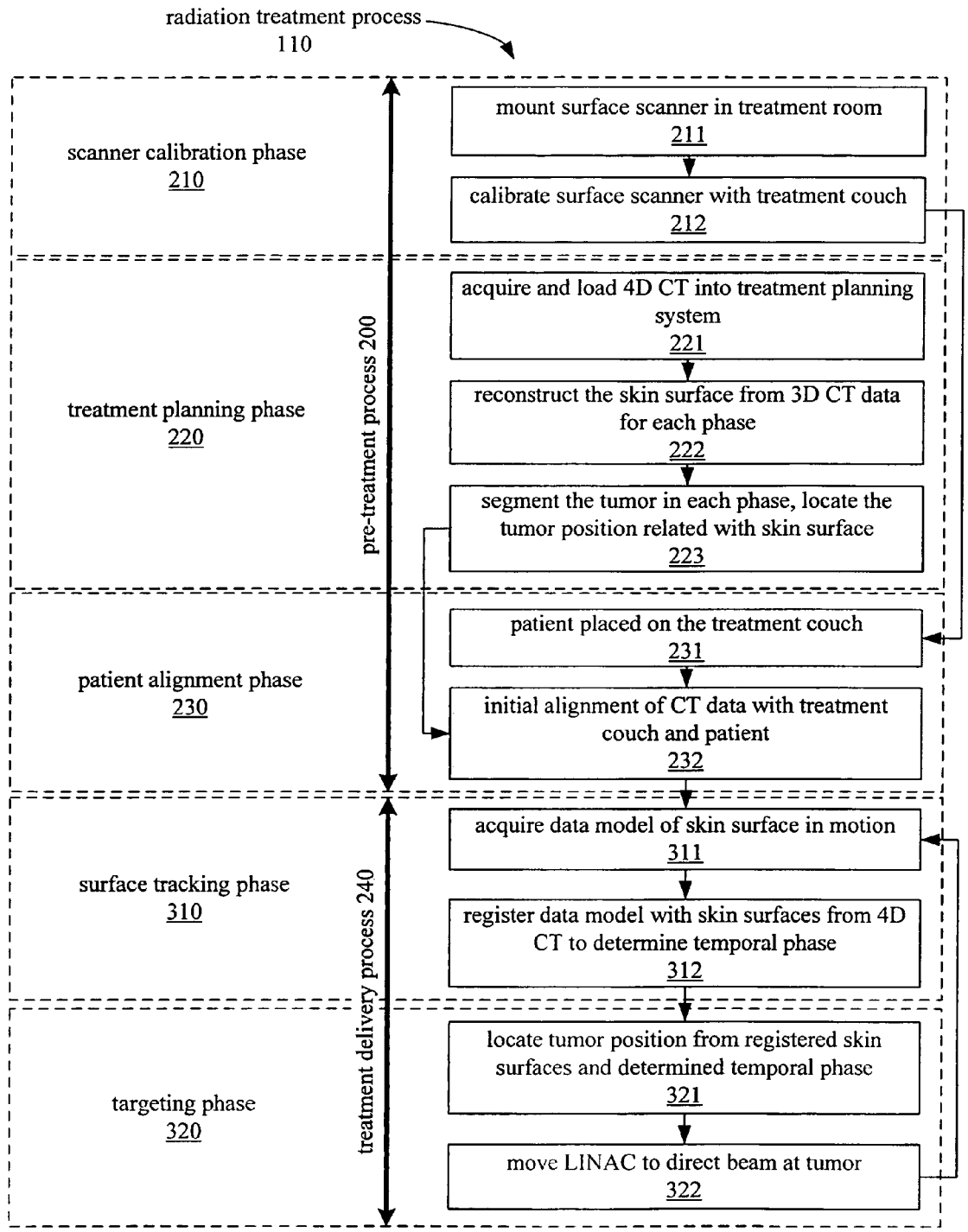
FIG. 1B is a flow chart illustrating a process of preparing for and delivering radiation treatment while tracking motion of a treatment target.

FIG. 1B is a flowchart illustrating a process of preparing for and delivering radiation treatment to a target within the body of a patient, while the location of the target is tracked using a system such as treatment delivery system 100, according to one embodiment of the invention. Radiation treatment process 110 includes pre-treatment process 200, followed by treatment delivery process 240. Pre-treatment process 200 further includes scanner calibration phase 210 and treatment planning phase 220, which are followed by patient alignment phase 230. During scanner calibration phase 210, a surface scanner is first mounted in the room where the radiation treatment is to take place, as provided in process block 211. Then, the surface scanner is calibrated with respect to a treatment couch in the treatment room, as provided in process block 212. In the treatment planning phase 220, four dimensional diagnostic data, such as 4D CT data, is acquired and loaded into a treatment planning system, as provided in process block 221. In the following block 222, a skin surface of the patient being treated is reconstructed from three-dimensional (3D) diagnostic data derived from the 4D diagnostic data. For example, 4D CT data may be considered as a series of 3D CT images each corresponding to a point in time. The 3D CT images can then be used to reconstruct the skin surface according to process block 222. In process block 223, a tumor within the patient's body is segmented, or reconstructed, from the CT data. In block 223, the location of the tumor is also determined relative to the skin surface. Following the completion of scanner calibration phase 210 and treatment planning phase 220, patient alignment phase 230 may begin. In patient alignment phase 230, the patient is first placed on the treatment couch, as provided in process block 231. Then, in block 232, the CT data is aligned with the treatment couch and the patient. In other words, a transformation is determined that relates the CT data to the patient and the treatment couch. Pre-treatment process 200 is followed by treatment delivery process 240, including surface tracking phase 310, which is followed by targeting phase 320. In surface tracking phase 310, a data model of the patient's skin surface is captured using the surface scanner. The skin surface may be in motion at the time of the capture, for example, as a result of the patient's respiratory cycle. In process block 312, the acquired data model is then registered with skin surfaces reconstructed from the 4D CT data in order to determine a temporal phase of the patient's respiratory cycle at the time the data model was acquired. Once block 312 has been completed, targeting phase 320 may begin. Targeting phase 320 begins with block 321, where the tumor position is located using the registered skin surfaces and the temporal phase previously determined in block 312. Once the location of the tumor has been determined, a LINAC may be moved so that its beam intersects the tumor. Blocks 311, 312, 321, and 322 of treatment delivery process 240 may be repeated so that the beam of the LINAC is continuously directed at the tumor for the duration of the treatment delivery process 240. Radiation treatment process 110 is described in more detail in the following paragraphs.

Figure 2:
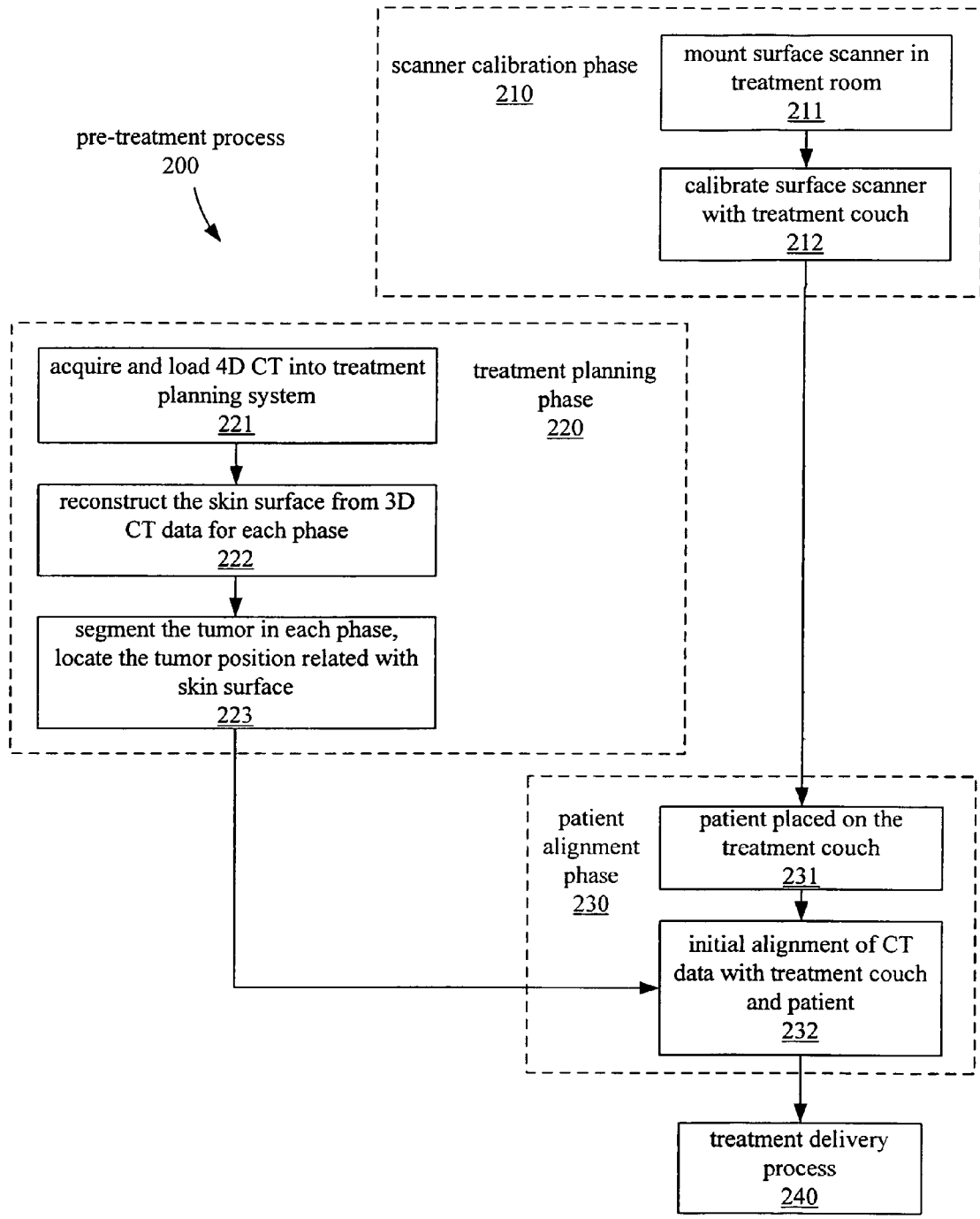
FIG. 2 is a flow chart illustrating a pre-treatment preparation process for radiation treatment using a treatment delivery system having motion tracking capabilities.

FIG. 2 is a flowchart illustrating a pre-treatment process 200 for preparing a system such as treatment delivery system 100 prior to a radiation treatment session of a patient, according to one embodiment of the invention. Pre-treatment process 200 may be part of radiation treatment process 110, as previously described. Pre-treatment process 200 includes three main phases: the scanner calibration phase 210, the treatment planning phase 220, and the patient alignment phase 230.

During the scanner calibration phase 210, a surface scanner such as surface scanner 102 is mounted in a treatment room. The surface scanner 102 may be mounted anywhere in the treatment room, so long as surface scanner 102 is mounted in an orientation that enables surface scanner 102 to acquire a data model of skin surface 105. In one embodiment, surface scanner 102 may be attached to a fixed mount, while in other embodiments, surface scanner 102 may be attached to a movable mount, such as a tracked robotic mount. After surface scanner 102 is mounted as described in process block 211, the surface scanner 102 is calibrated with respect to the treatment couch, as described in process block 212. Calibration may be performed by determining the transformation from the imaging plane or the imaging volume of the surface scanner 102 to the treatment couch 109.

The treatment planning phase 220 may take place before, after, or concurrently with the scanner calibration phase 210. The treatment planning phase 220 begins with process block 221, where 4D CT data of the patient to be treated is acquired and loaded into a treatment planning system, according to one embodiment of the invention. In other embodiments, the data may not necessarily be 4D CT data, but may also be any data that describes the subject of the treatment in multiple dimensions. For example, the data may be a series of 3D CT scans, or a series of 3D images obtained by methods other than CT. The 4D CT data is acquired so that it includes the portion of the patient's anatomy to which treatment will be administered. The 4D CT data includes a three dimensional representation of the patient's anatomy that is captured over time, so that changes in the patient's anatomy over time are also captured. For example, the shape of the patient's body may change over time as the patient breathes. These temporal changes corresponding to phases in the patient's respiratory cycle may be captured by the 4D CT scan. After 4D CT data is acquired, the data is loaded into the treatment planning system. The treatment planning system into which the 4D CT data is loaded may be a system that is configured to execute treatment planning phase 220. For example, the treatment planning system may be a computer having software installed that executes the stages 221, 222, and 223 of treatment planning phase 220. Thus, loading 4D CT data into the treatment planning system may simply entail making the data accessible to the treatment planning system on a storage medium, such as an optical or magnetic disk.

After the 4D CT data is loaded into the treatment planning system as provided in process block 221, execution proceeds to process block 222, where the treatment planning system reconstructs the skin surface of the patient from the 4D CT data. The 4D CT data may be considered as a series of three-dimensional (3D) CT images each corresponding to a point in time. Each of these 3D CT images can then be used to reconstruct skin surfaces corresponding respectively to those points in time. The points in time corresponding to the reconstructed skin surfaces can then be considered as temporal phases in the patient's respiratory cycle. Thus, the result of process block 222 is data representing a series of reconstructed skin surfaces corresponding to temporal phases in the patient's respiratory cycle.

In process block 223, the tumor within the patient is segmented, or reconstructed, for each temporal phase from the CT data corresponding to the temporal phase. The reconstructed data model of the tumor is then related with the reconstructed skin surface corresponding to the same temporal phase. In other words, for each temporal phase, the orientation and position of the tumor with respect to the reconstructed skin surface for that temporal phase is determined.

After completion of the scanner calibration phase 210 and the treatment planning phase 220, the pre-treatment process 200 continues to the patient alignment phase 230. The patient alignment phase 230 may begin with the placement of patient 106 on the treatment couch 109, as provided in process block 231. Execution then continues to process block 232, where initial alignment of the patient is performed. The goal of process block 232 is to determine the appropriate transformations between the acquisition plane (or volume) of the surface scanner and the CT data. In other words, the goal is to align the CT image and surface scan so that a similarity match can later be determined between them. This goal may be accomplished using landmark-based registration. For example, while patient 106 is lying on treatment couch 109, the body of patient 106 may contain one or more landmarks such as a spine, other bones, or implanted fiducials. The locations of the landmarks while the patient 106 is lying on treatment couch 109 can be resolved using such techniques as X-ray or ultrasound. The landmarks also appear in the CT images. Thus, the CT images and the actual patient 106 can be aligned in three-dimensional space by matching the locations of the landmarks. Since the patient 106 is stationary with respect to treatment couch 109, the transformation between the CT images and the treatment couch can be determined. Then, since the transformation between the treatment couch 109 and the acquisition plane or volume of surface scanner 102 had previously been determined in process block 212, the transformation between the acquisition plane or volume of the surface scanner 102 and the CT images can also be determined. As a result of the alignment, the acquisition plane or volume of the surface scanner 102 may be aligned with the CT images in three-dimensional space, such that when the surface scanner 102 acquires skin surface 105, the acquired skin surface may be effectively compared with the skin surfaces reconstructed from CT data in process block 222 to produce a similarity measurement. After the alignment of the CT data with the treatment couch and patient, the treatment delivery process 240 may begin.

Figure 3:
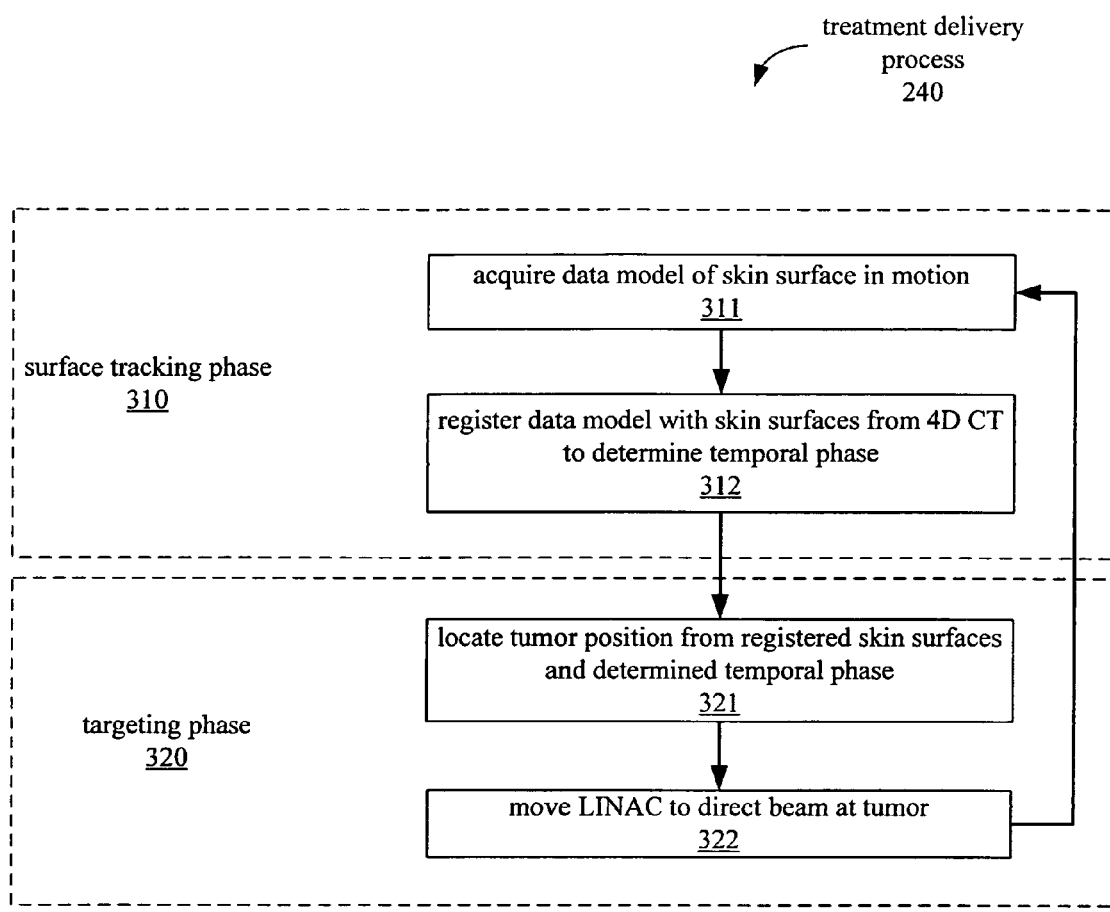
FIG. 3 is a flow chart illustrating stages in a treatment delivery phase using a treatment delivery system having motion tracking capabilities.

According to one embodiment of the invention, treatment delivery process 240 may be conducted as part of radiation treatment process 110, as illustrated in FIG. 3. Treatment delivery process 240 includes surface tracking phase 310, which is followed by targeting phase 320. In the surface tracking phase 310, a data model of the skin surface of the patient is first acquired in process block 311. The data model is then registered with skin surfaces reconstructed from 4D CT data of the patient in order to determine the temporal phase of the respiratory cycle at the time the data model was captured. Following process block 312, execution of process block 321 in the targeting phase 320 takes place. In process block 321, the location and orientation of a tumor or other volume within the patient is determined using previously acquired 3D CT data corresponding to the temporal phase identified in process block 312. Once the position of the tumor has been identified, a linear accelerator (LINAC) may be moved so that its beam intersects a target within the tumor or other volume, as provided in process block 322. Process blocks 311, 312, 321, and 322 may be repeated for the duration of the treatment delivery process 240 so that the location and orientation of the tumor may be continuously tracked and targeted by the LINAC. The process is described in further detail below.

Figure 4A:
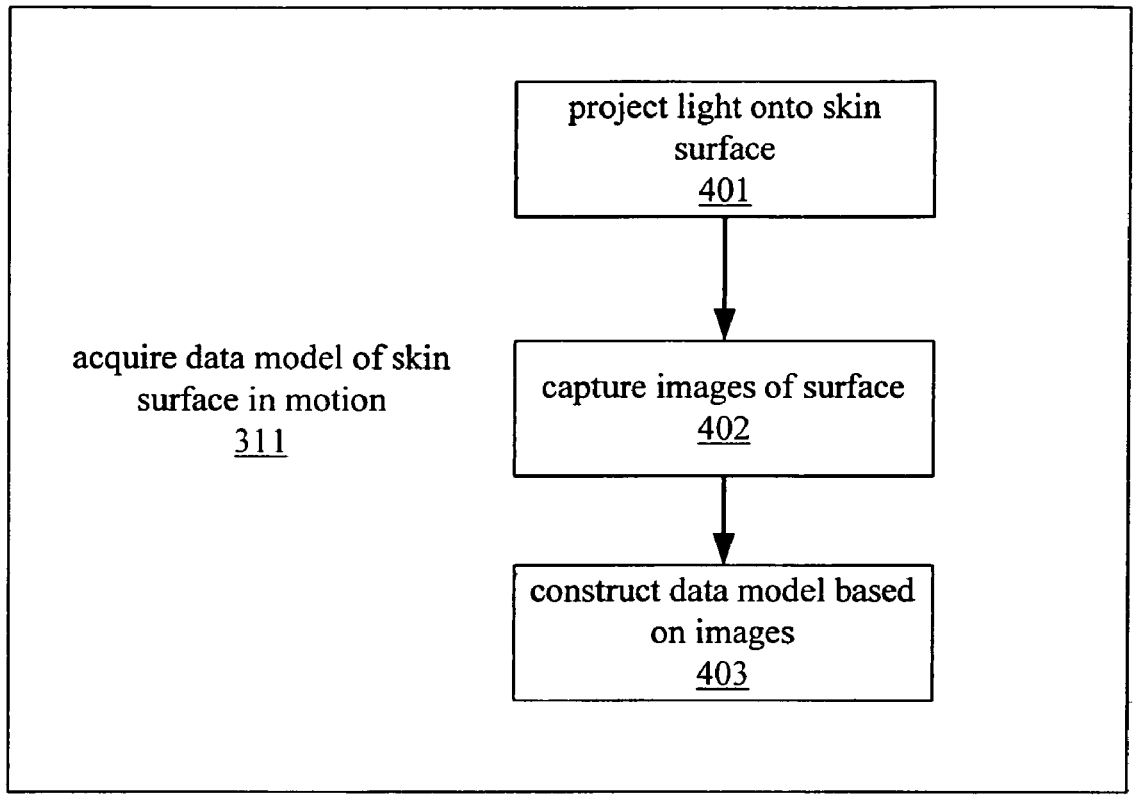
FIG. 4A is a flow chart illustrating stages in a process for acquiring a data model of a skin surface.

Surface tracking phase 310 begins with process block 311, which provides for the acquisition of a data model of a skin surface of the patient, such as skin surface 105 of the body of a patient 106. Surface scanner 102 may perform the procedures of acquiring a data model of the skin surface in motion, as provided by process block 311. As illustrated in FIG. 4A, these procedures, according to one embodiment, include projecting light onto the skin surface 401, capturing images of the surface 402, and constructing a data model based on the images 403. As previously mentioned, surface scanner 102 may be a system such as a laser scanning system or a digital photogrammetry system.

Figure 4B:
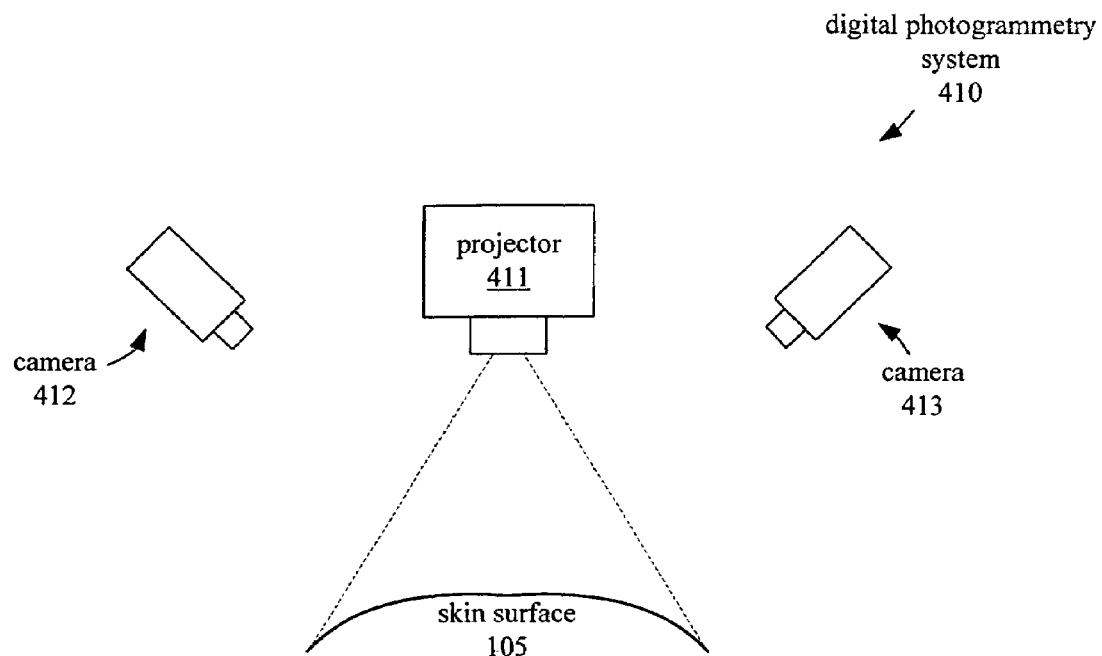
FIG. 4B is a block diagram illustrating components of a digital photogrammetry system.

FIG. 4B illustrates components of a digital photogrammetry system that may be used as surface scanner 102, according to one embodiment of the invention. Digital photogrammetry system 410 includes projector 411 and cameras 412 and 413. The digital photogrammetry system 410 may begin the skin surface acquisition process by projecting light onto the skin surface 105, as provided in process block 401, using projector 411. In one embodiment, projector 411 may project a pattern such as a pattern of evenly spaced dots onto the skin surface 105. Alternatively, different types of light patterns, such as lines or a grid, may also be projected onto the skin. While the light pattern is being projected onto skin surface 105, cameras 412 and 413, which may be situated at different angles with respect to skin surface 105, may acquire images of skin surface 105 by capturing the light reflected from skin surface 105 as provided in process block 402. The images of skin surface 105 captured by cameras 412 and 413 may then be used to triangulate positions of points on the skin surface, since the images are taken from different angles. The points can then be assembled into a three-dimensional model of the skin surface in accord with process block 403.

Figure 4C:
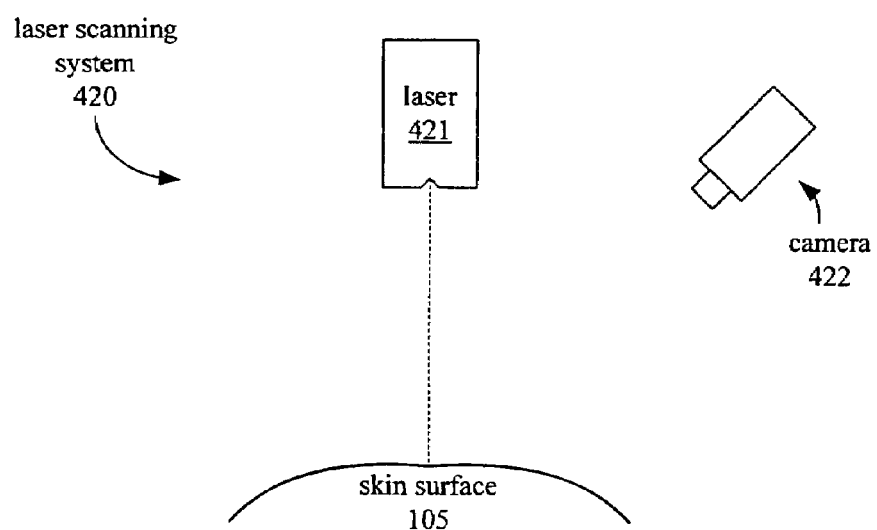
FIG. 4C is a block diagram illustrating components of a laser scanning system.

In an alternative embodiment, surface scanner 102 may be a laser scanning system, such as laser scanning system 420 depicted in FIG. 4C. Laser scanning system 420 may include a laser 421 and a camera 422. Laser scanning system 420 initiates the acquisition of skin surface 105 by projecting a point of laser light in a known direction onto skin surface 105 using laser 421, as provided in process block 401. Camera 422 may then be used to capture the location of the resulting point of laser light reflected from skin surface 105 in accord with process block 402. Subsequently, laser 421 may project a point of laser light onto a different location on skin surface 105, after which camera 422 may again capture the location of the point of laser light. Thus, process blocks 401 and 402 are repeated for every point on skin surface 105 to be acquired. In this manner, camera 422 may operate to capture a series of points on skin surface 105. The location of each of these points in three-dimensional space can then be triangulated using the known direction of the projected laser beam and the location of the point as seen and recorded by camera 422. The points, now having known coordinates in three-dimensional space, can subsequently be assembled into a three-dimensional data model of skin surface 105, as provided in process block 403.

In other embodiments, methods other than digital photogrammetry or laser triangulation may be used to acquire a data model of the skin surface. For example, the skin surface may be acquired using a method similar to time-of-flight laser range finding. Alternative embodiments may also use other techniques capable of acquiring the skin surface without actively projecting light onto the skin surface.

During the acquisition of skin surface 105, skin surface 105 may be in motion. For example, skin surface 105 may rise and fall with the respiratory cycle of patient 106. Thus, the acquisition time required for surface scanner 102 to acquire a complete scan of the skin surface 105 may be sufficiently brief so that the scan data and resulting data model is not significantly affected by the motion of skin surface 105.

Once the scan of skin surface 105 is completed, the acquired data model of skin surface 105 is registered with 4D CT data 103 by processor 101. The goal of the registration process is to identify one or more CT surfaces, which are three-dimensional images of the skin surface reconstructed from the 4D CT data 103, that are most similar to the acquired skin surface. A temporal phase corresponding to the acquired skin surface may then be determined based on which of the CT surfaces are identified as most closely matching the acquired skin surface.

Figure 5A:
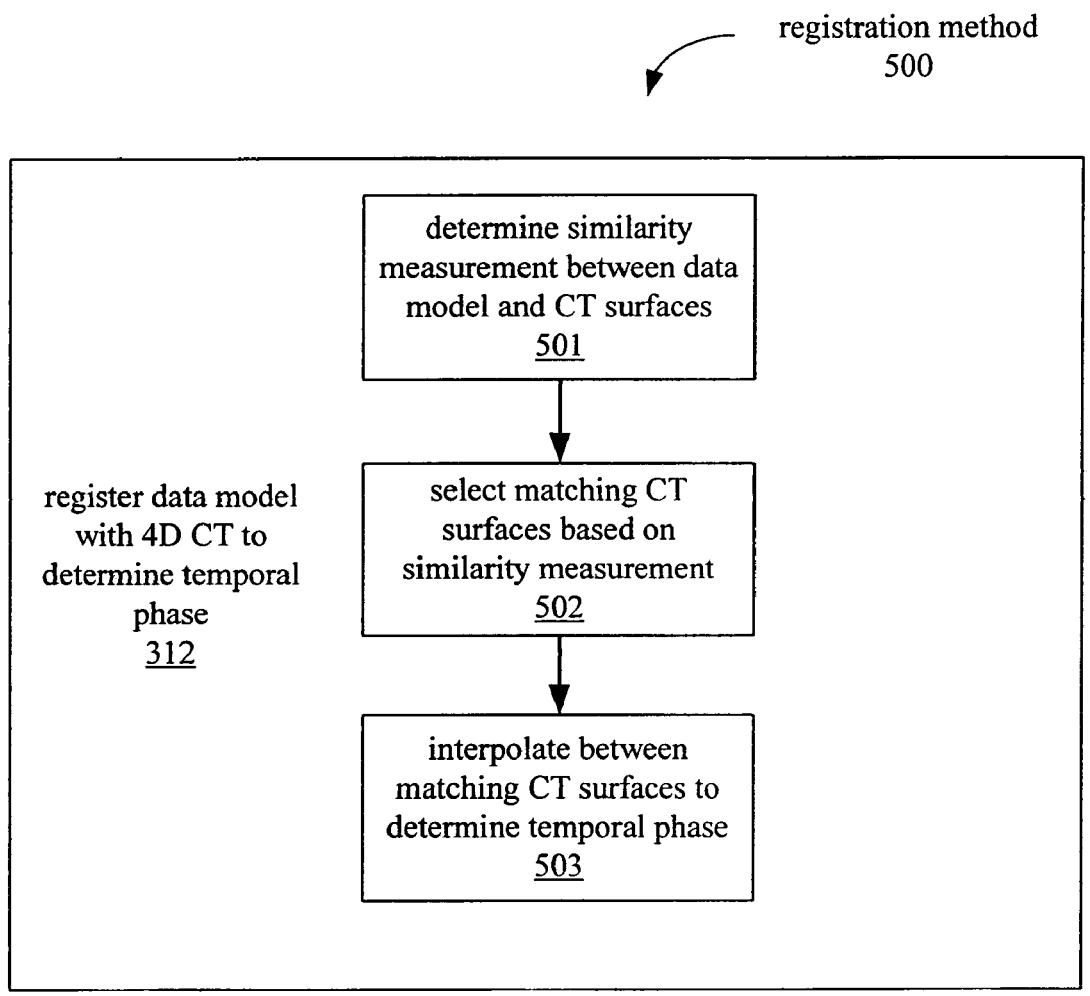
FIG. 5A is a flow chart illustrating stages in a process for registering a data model of a skin surface with four-dimensional computed tomography (4D CT) data.
Figure 5B:
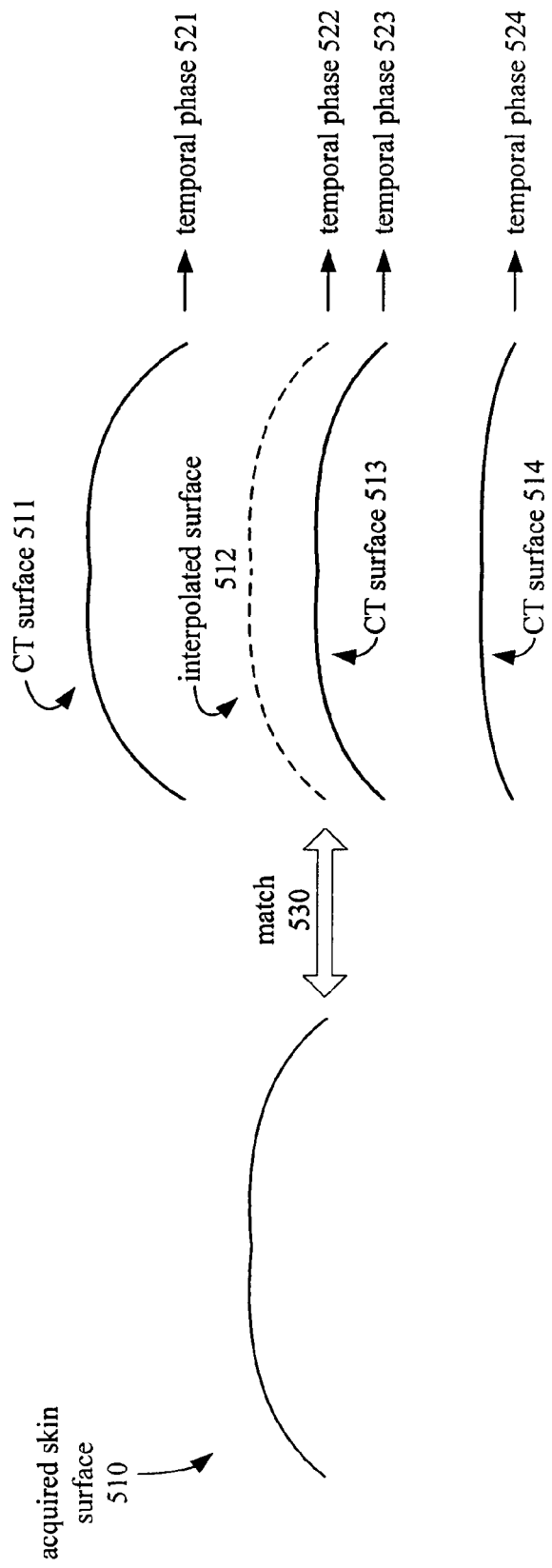
FIG. 5B illustrates a process for registering an acquired skin surface with surfaces reconstructed from 4D CT data.

FIG. 5A illustrates a process according to one embodiment for registering the acquired data model of the skin surface with the CT surfaces in order to determine a temporal phase of the patient's respiratory cycle, as provided in process block 312. FIG. 5B illustrates a series of three CT surfaces, 511, 513, and 514, that are to be compared with acquired skin surface 510. CT surfaces 511, 513, and 514 correspond to temporal phases 521, 523, and 524, respectively, and may have been constructed from empirically sampled data. For example, CT surfaces 511, 513, and 514 may have been reconstructed from data acquired from a 4D CT scanner performing a scan on patient 106. Registration method 500 begins with process block 501, where a similarity measurement is determined between the data model of the skin surface and the CT surfaces. For example, a similarity measurement may be calculated between two images, the first derived from a CT surface and the second derived from the data model of the skin surface. The similarity measurement may be calculated by subtracting corresponding pixel values of the first image from the second image to form a difference image, then applying a pattern intensity function to the difference image. The calculation of similarity measurements is known in the art, therefore a more detailed description of the process for deriving a similarity measurement is not provided. Similarity measurements are described in detail in U.S. Pat. No. 7,187,792, U.S. patent application Ser. Nos. 10/652,786, and 11/281,106. In accord with process block 501, a similarity measurement may be calculated between acquired skin surface 510 and each of CT surfaces 511, 513, and 514. In other embodiments, a similarity measurement need not be calculated for all of the available CT surfaces. After the similarity measurement calculations, one or more of the CT surfaces that most closely matches the data model is identified based on the resulting similarity measurement, as provided in process block 502. For example, two CT surfaces, 511 and 513, may be identified that most closely match the acquired skin surface 510. Neither of CT surfaces 511 or 513 may match acquired skin surface 510 exactly, since acquired skin surface 510 may have been acquired during a temporal phase in the patient's respiratory cycle that is different from the temporal phases associated with the two identified surfaces. For example, acquired skin surface 510 may have been acquired during a temporal phase between temporal phases 521 and 523. Thus, following the completion of process block 502, interpolation may be performed to generate a surface intermediate between CT surfaces 511 and 513 that more closely matches acquired skin surface 510, as provided in process block 503. The interpolated skin surface may also correspond to a temporal phase more closely matching the temporal phase of acquired skin surface 510. According to one embodiment, several intermediate surfaces may be generated by interpolation between the identified skin surfaces. For example, ten surfaces (not pictured) may be interpolated between CT surfaces 511 and 513 which had been identified as most similar to acquired skin surface 510. Of these, interpolated surface 512 may match acquired skin surface 510 with the best similarity measurement, as indicated by the "match" arrows 530. Thus, the temporal phase 522 corresponding to interpolated surface 512 may be identified as the temporal phase during which acquired skin surface 510 was captured.

The result of registration method 500 is that the temporal phase of the patient's respiratory cycle, as of the time of the surface scan, is identified. This temporal phase can later be used with the 4D CT data 103 to determine the position of a target 107 with respect to the skin surface 105.

Figure 6A:
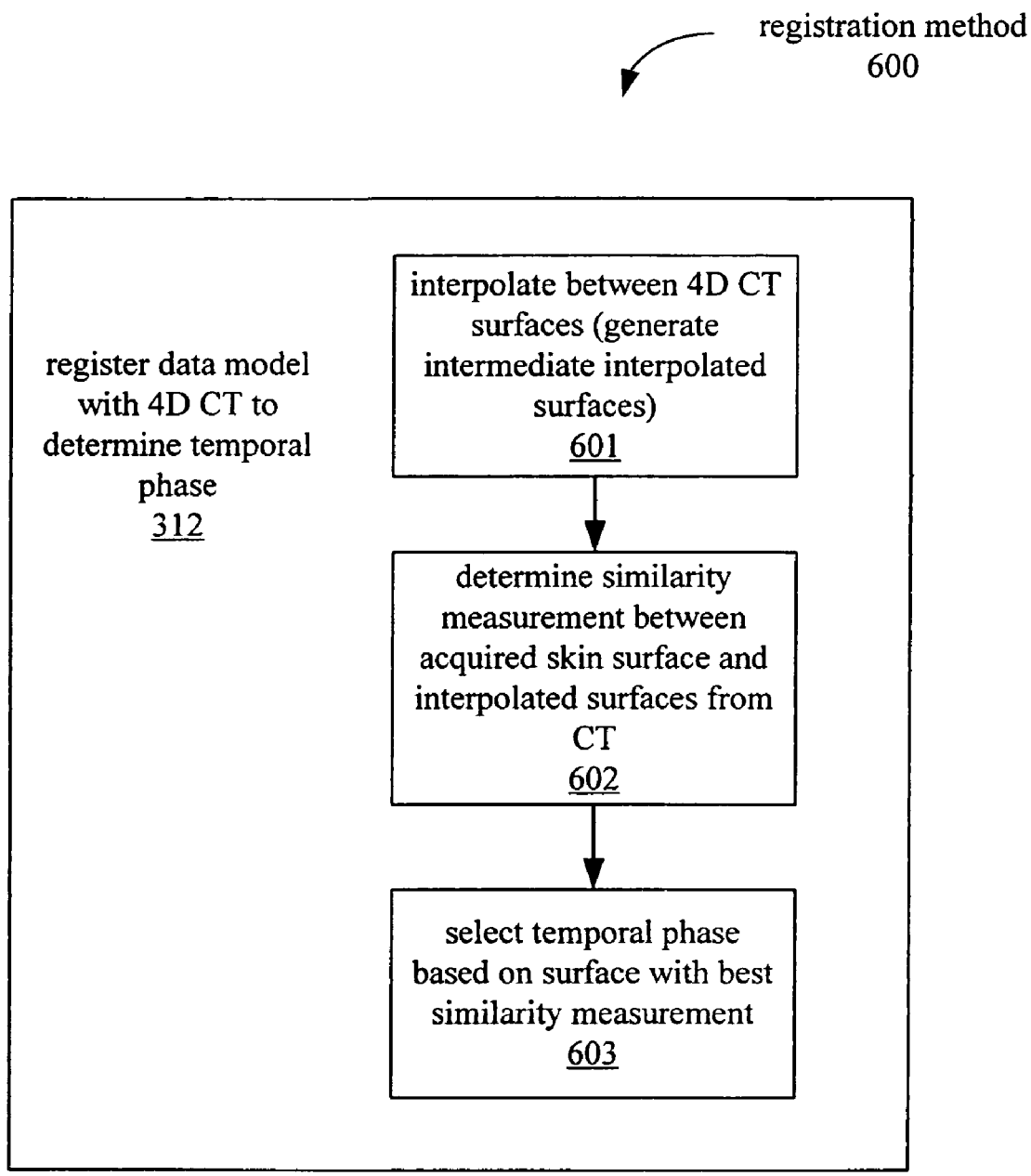
FIG. 6A is a flow chart illustrating stages in a process for registering a data model of a skin surface with four-dimensional computed tomography data.
Figure 6B:
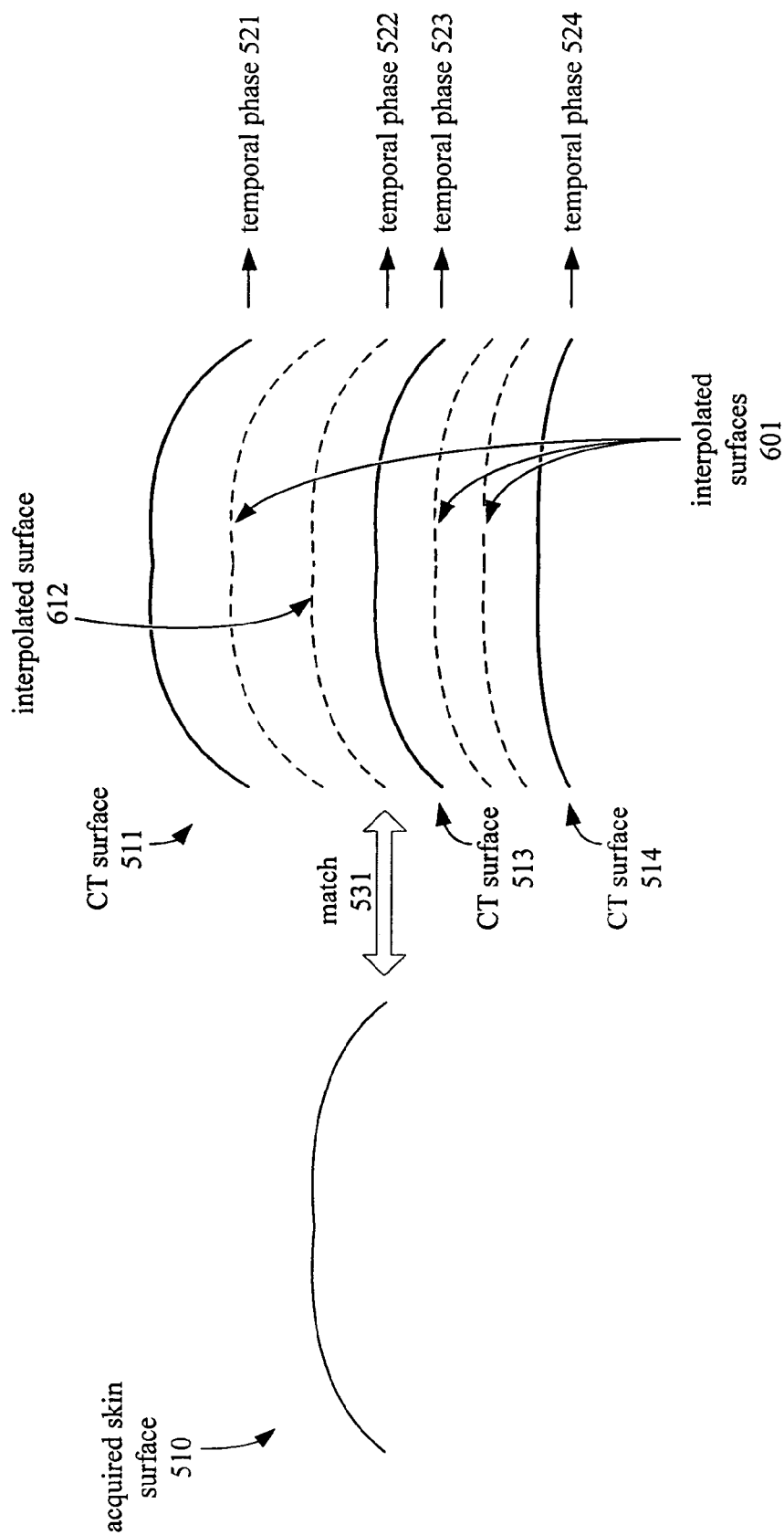
FIG. 6B illustrates a process for registering an acquired skin surface with surfaces reconstructed from 4D CT data.

An alternative embodiment for registering the acquired skin surface with the CT surfaces in order to determine a temporal phase of the patient's respiratory cycle, as provided in process block 312 is illustrated in FIG. 6A. FIG. 6B illustrates a series of three CT surfaces, 511, 513, and 514, that are to be compared with acquired skin surface 510. CT surfaces 511, 513, and 514 correspond to temporal phases 521, 523, and 524, respectively. Registration method 600, as illustrated in FIG. 6A, begins with process block 601, which provides for generation of intermediate surfaces by interpolation between the CT surfaces, such as CT surfaces 511, 513, and 514, reconstructed from the 4D CT data 103. For example, during execution of process block 601, interpolated surfaces 601 and interpolated surface 612 are generated. Interpolated surfaces 601 and interpolated surface 612 correspond to intermediate temporal phases between the temporal phases 521, 523, and 524 corresponding to CT surfaces 511, 513, and 514, respectively. After the generation of the interpolated surfaces 601 and 612, execution proceeds to process block 602, where a similarity measurement is determined between acquired skin surface 510 and each of the CT surfaces 511, 513, and 514, and the interpolated surfaces 601 and 612. In other embodiments, calculation of a similarity measurement may not be required for all of the CT surfaces and interpolated surfaces. After the similarity measurements have been calculated, execution proceeds to process block 603, where the surface having the best similarity measurement with the acquired skin surface 510 is identified. For example, interpolated surface 612 may be identified as having the best similarity measurement with acquired skin surface 510, as indicated by the "match" arrows 531. The temporal phase 522 corresponding to interpolated surface 612 may then be identified as the temporal phase during which acquired skin surface 510 was captured.

Figure 7:
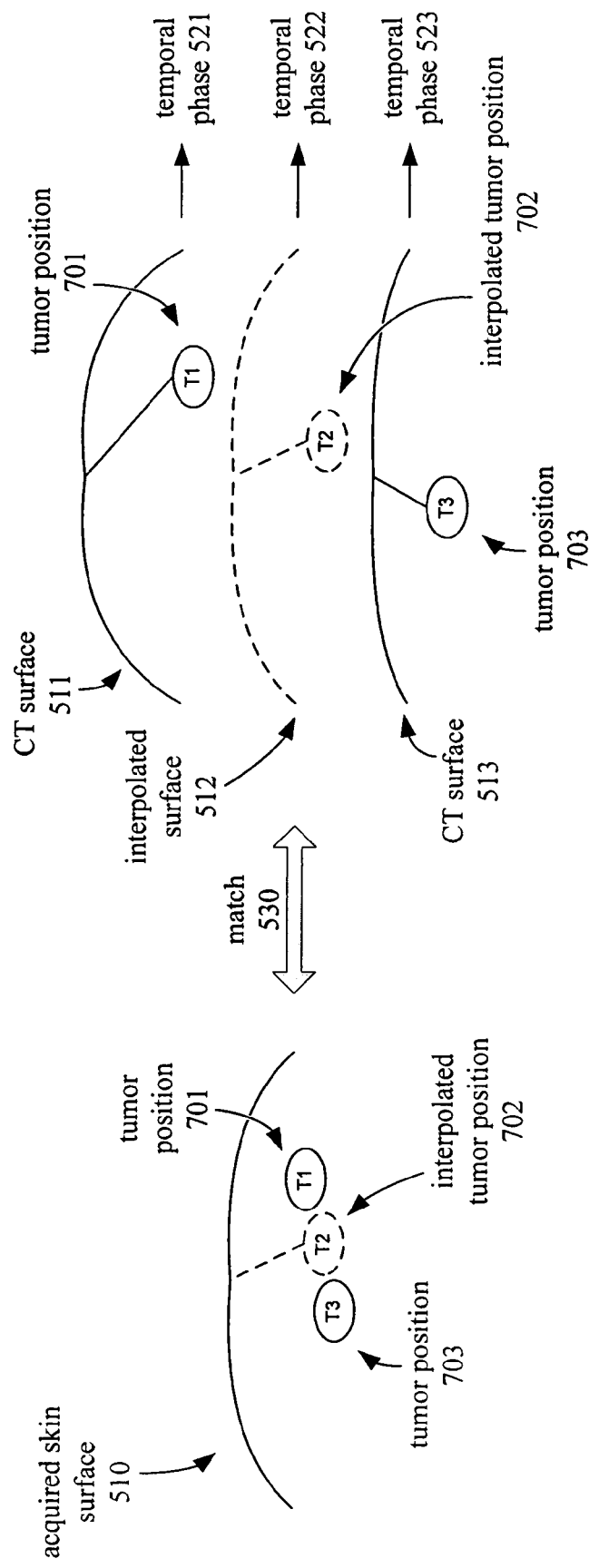
FIG. 7 illustrates a process for determining a tumor position relative to a skin surface by interpolation.

FIG. 7 illustrates various surfaces along with corresponding tumor positions, according to one embodiment of the invention. Other embodiments of the invention may not identify positions of a tumor, but may include positions of other objects, such as stones or lesions. For a tumor position corresponding to a CT surface, such as tumor position 701 corresponding to CT surface 511, the tumor position 701 identifies the location of the tumor relative to the CT surface 511 at the time of temporal phase 521. Tumor position 701 may identify a different location relative to the skin surface as the location of the tumor than tumor position 703 because the location of the tumor may change between different temporal phases. For example, the tumor may move as a result of the patient's breathing or heartbeat.

Thus, if temporal phase 521 is identified in process block 312 as the temporal phase most closely matching the temporal phase at which the acquired skin surface 510 was captured, then tumor position 701 can be used to locate the tumor relative to CT surface 511, as provided in process block 321. Since transformations between the CT data 103, which includes CT surface 511, and the treatment couch 109 have been determined during patient alignment phase 230, the transformations can be used to locate the tumor in real space.

According to one embodiment of the invention, a tumor position can be interpolated from two or more tumor positions, such as tumor positions 701 and 703. This interpolation may take place during the execution of process block 321. Tumor position 701 may indicate the location of the tumor at time T1, while tumor position 703 may indicate the location of the tumor at time T3. Thus, in order to determine the location of the tumor at time T2 intermediate between times T1 and T3, a tumor position 702 is interpolated between tumor positions 701 and 703. More specifically, acquired skin surface 510 may be matched with interpolated surface 512, and the temporal phase of acquired skin surface 510 may be determined to be temporal phase 522 corresponding to interpolated surface 512. In order to determine the location of the tumor in relation to acquired skin surface 510 or interpolated surface 512, an additional tumor location can be interpolated from existing tumor positions 701 and 703. For example, interpolated tumor position 702 corresponding to interpolated surface 512 may be interpolated from the tumor positions 701 and 703, which correspond to CT surfaces 511 and 513 from which interpolated surface 512 was interpolated. Once the location of tumor position 702 relative to interpolated surface 512 has been determined, tumor position 702 can be used to locate the tumor in real space relative to the patient's skin surface using the transformations determined in patient alignment phase 230.

After the tumor position has been located in real space, processor 101 may direct robotic arm 108 to move so that the beam of LINAC 104 intersects a target 107, as provided in process block 322. The process of locating the tumor from the acquired skin surface 510 and 4D CT data 103, then moving the LINAC 104 so that its beam intersects the target 107 may be repeated so that the beam of LINAC 104 constantly intersects the target 107 for the duration of the treatment phase, despite the movement of target 107 due to the respiration, heartbeat, or other movements of patient 106.

Alternatively, treatment delivery system 100 may be a type of system other than a robotic arm-based system. For example, treatment delivery system 100 may be a gantry-based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry-based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Certain embodiments may be implemented as a computer program product that may include instructions stored on a computer-readable medium. These instructions may be used to program a general-purpose or special-purpose processor to perform the described operations. A computer-readable medium includes any mechanism for storing or transmitting information in a form (e.g., software, processing application) readable by a computer. The computer-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the computer-readable medium is stored on and/or executed by more than one computer system. In addition, the information transferred between computer systems may either be pulled or pushed across the communication medium connecting the computer systems.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   acquiring a data model of a skin surface of a body based on light reflected from the skin surface, wherein the skin surface is subject to movement;
   registering the data model of the surface with four-dimensional diagnostic imaging data to determine a matching temporal phase; and
   determining a position of a target within the body based on the matching temporal phase from the four-dimensional diagnostic imaging data.

2. The method of claim 1, wherein the acquired data model of the skin surface of the body is an indicator of respiratory motion.

3. The method of claim 1, further comprising projecting light onto the surface of the body.

4. The method of claim 3, wherein the projected light is laser light.

5. The method of claim 1, wherein said acquiring of the data model of the surface comprises:
   capturing a plurality of images of the surface; and
   constructing the data model of the surface based on the captured plurality of images.

6. The method of claim 1, wherein said registering the data model of the surface with the four-dimensional diagnostic imaging data comprises comparing the data model with a plurality of images of the surface from the four-dimensional diagnostic imaging data, wherein each of the plurality of images corresponds to a temporal phase of the movement.

7. The method of claim 6, wherein at least one of the images is constructed from empirically sampled data.

8. The method of claim 6, wherein at least one of the images corresponding to an intermediate temporal phase is interpolated from empirically sampled data.

9. The method of claim 1, wherein registering the data model of the surface with the four-dimensional diagnostic imaging data comprises:
   determining a similarity measurement between the data model and a set of data from the four-dimensional diagnostic imaging data; and
   selecting the matching temporal phase corresponding to the set of data based on the similarity measurement.

10. The method of claim 1, wherein the four-dimensional diagnostic imaging data is four-dimensional computed tomography (CT) data.

11. The method of claim 1, wherein the four-dimensional diagnostic imaging data comprises a plurality of three-dimensional images, where each of the plurality of three-dimensional images represents a different point in a motion cycle.

12. The method of claim 1, further comprising moving a linear accelerator (LINAC) to direct a radiation beam at the target in response to the determined position of the target.

13. The method of claim 12, wherein moving the linear accelerator (LINAC) comprises moving a robotic arm coupled with the LINAC.

14. The method of claim 12, wherein moving the linear accelerator (LINAC) comprises moving a gantry coupled with the LINAC.

15. The method of claim 14, wherein the linear accelerator (LINAC) is mounted on a gimbal.

16. An apparatus, comprising:
   a processor configured to acquire a data model of a skin surface of a body based on light reflected from the skin surface, wherein the skin surface is subject to movement, the processor further configured to register the data model of the surface with four-dimensional diagnostic imaging data to determine a matching temporal phase, the processor further configured to determine a position of a target within the body based on the matching temporal phase from the four-dimensional diagnostic imaging data.

17. The apparatus of claim 16, further comprising a light projector coupled with the processor, the light projector configured to project light onto the surface of the body.

18. The apparatus of claim 16, further comprising a camera coupled with the processor, the camera configured to capture a plurality of images of the surface, wherein the processor is further configured to construct the data model of the surface based on the captured plurality of images.

19. The apparatus of claim 16, wherein the processor is further configured to register the data model of the surface with the four-dimensional diagnostic imaging data by comparing the data model with a plurality of images of the surface from the four-dimensional diagnostic imaging data, wherein each of the plurality of images corresponds to a temporal phase of the movement.

20. The apparatus of claim 19, wherein at least one of the images is constructed from empirically sampled data.

21. The apparatus of claim 19, wherein at least one of the images corresponding to an intermediate temporal phase is interpolated from empirically sampled data.

22. The apparatus of claim 19, wherein the four-dimensional diagnostic imaging data is four-dimensional computed tomography (CT) data.

23. The apparatus of claim 19, wherein the four-dimensional diagnostic imaging data comprises a plurality of three-dimensional images, where each of the plurality of three-dimensional images represents a different point in a motion cycle.

24. The apparatus of claim 19, wherein the processor is further configured to move a linear accelerator (LINAC) to direct a radiation beam at the target in response to the determined position of the target.

25. The apparatus of claim 16, wherein the processor is further configured to register the data model of the surface with the four-dimensional diagnostic imaging data by determining a similarity measurement between the data model and a set of data from the four-dimensional diagnostic imaging data and selecting the matching temporal phase corresponding to the set of data based on the similarity measurement.

* * * * *